(12) United States Patent
Pagedas

(10) Patent No.: US 6,475,229 B1
(45) Date of Patent: Nov. 5, 2002

(54) MOLDABLE CRIMPABLE SUTURE THREAD AND METHOD FOR MAKING SAME

(75) Inventor: Anthony C. Pagedas, Greendale, WI (US)

(73) Assignee: Ancel Surgical R&D, Inc., Greendale, WI (US)

( * ) Notice: Subject to any disclaimer, the term of this patent is extended or adjusted under 35 U.S.C. 154(b) by 0 days.

(21) Appl. No.: 09/570,755

(22) Filed: May 15, 2000

(51) Int. Cl.[7] ................................................ A61B 17/04

(52) U.S. Cl. ........................................................ 606/228

(58) Field of Search .................................. 606/228, 232

(56) References Cited

U.S. PATENT DOCUMENTS

| | | | | |
|---|---|---|---|---|
| 4,932,962 A | * | 6/1990 | Yoon et al. | 606/224 |
| 5,413,585 A | * | 5/1995 | Pagedas | 606/151 |
| 5,628,756 A | * | 5/1997 | Barker et al. | 606/139 |
| 5,814,056 A | * | 9/1998 | Prosst et al. | 24/16 PB |
| 6,015,428 A | * | 1/2000 | Pagedas | 606/232 |

\* cited by examiner

Primary Examiner—Gary Jackson
(74) Attorney, Agent, or Firm—Ryan Kromholz & Manion, S.C.

(57) ABSTRACT

An integrally molded, one-piece combination suture thread and crimpable lock opening whereby at least one crimpable opening is disposed along the thread length. The thread may be used with a surgical needle. Both a mono-ply and multiple suture thread and crimpable opening is disclosed.

9 Claims, 5 Drawing Sheets

MOLDABLE CRIMPABLE SUTURE THREAD AND METHOD FOR MAKING SAME

BACKGROUND OF THE INVENTION

The need for this invention arises from surgical practice, particularly surgical practice using laparoscopic instruments involving small incisions, with a television camera inserted in one of the incisions to view the field of the operation inside the patient and surgical instruments inserted in other incisions and manipulated from outside the patient'body using a TV screen visualization, usually enlarged, to guide the work.

Anything that can reduce the number of steps to be performed in such an operation can markedly reduce the stress, both on the patient and on the doctor. Surgeons performing such operations are under considerable stress because remote manipulation using TV for visualization, rather than seeing the site of the operation directly requires the learning of a great many techniques that are radically different from those performed when the surgical site is open to view. These include indirect hand-eye coordination, and cooperation between surgeons to place and secure sutures.

The placing of sutures during a laparoscopic procedure typically requires two surgeons to cooperate in a multi-step process performed with multiple surgical instruments to manipulate the needle and the suture and pass it back and forth from one to the other, cooperation in tying the knot, etc. This invention arose from experiencing the difficulty of such manipulations.

Additionally, coagulation and clips, such as "hemo clips", have reduced many of the needs for endoscopic suturing. However, when one considers the need to suture repair ovaries, uterus, seromuscular defects, enterotomies, systomies, pelvic defects, various suspension procedures i.e. vaginal vault and sacrospinous, one must realize there is a continual need to keep the art of endoscopic suturing to the forefront. The endoscopic suturing must be so simple that it be easily learned, hence easily remembered. The learning curve in endoscopic suturing is inversely proportional to the number of steps required to do the suturing; i.e. the fewer steps required the easier it is to learn and teach the endoscopic suturing technique. It is the purpose of the present invention to provide a structure, which makes it easier to learn and teach an endoscopic suturing technique.

U.S. Pat. No. 5,413,585 and allowed application, Ser. No. 09/089,916, filed Jun. 3 1998 and assigned to the assignee of the present application, are believed, presently, to be the closest prior art references.

SUMMARY OF THE INVENTION

The present invention is an integrally molded, one-piece, combination suture thread and crimpable lock opening, and is preferably used with a suture needle. A least one crimpable ring is integrally molded with a mono-filament suture thread so that a crimpable opening is presented in the suture thread. The suture thread and crimpable opening is made of a material that is easily molded, yet is strong when cured. Further, the material must be biologically compatible with the surgical application in which it is to be used. The major consideration given to the type of material chosen is the tolerance of the human body to fairly long exposure to the presence of this material. Materials that the human body can tolerate, or an animal body can tolerate should this device be used on non-humans, should be chosen. Examples of suitable material include polygalaxon and DEXON monofilament. Accordingly, the needle may, after passing through the desired tissue to be sutured, be drawn through the crimpable lock opening a distance suitable to the surgeon making the stitch, and then the crimpable lock opening is crimped with a crimping tool known in the surgical art, thereby locking the suture thread in place without the necessity of tying a knot. In the preferred embodiment, the molded suture and crimpable lock opening is integrally formed, while the needle is attached to the suture thread either permanently or impermanently in a known way, as for example "pop off" needles. The crimpable lock opening is of a diameter slightly larger than the diameter of the suture thread, so that the suture thread may initially pass through the opening. When the medical practitioner desires to create a securement at a location along the suture thread, the crimpable ring surrounding and forming the lock opening, is crimped around the diameter of the suture thread.

Alternatively, the present invention may be described as a molded, one-piece suture having a plurality of laterally spaced, integrally molded, crimpable openings along the suture thread length.

In another embodiment, the mono-ply, integrally molded suture and crimpable openings of the previously disclosed embodiments may be covered with a plurality of filaments to form a plaited, multi-ply structure.

In yet another embodiment, an integrally molded suture thread may include a plurality of crimpable openings wherein the openings may be disposed in a superposed configuration. A stacked or superposed configuration allows an individual crimpable opening to be accessed and crimped independently of another, while allowing the practitioner to place multiple sutures in the same vicinity.

In still another embodiment, the suture thread, having a plurality of superposed crimpable openings, may be covered with a plurality of filaments to form a plaited, multi-ply structure.

DETAILED DESCRIPTION

Although the disclosure hereof is detailed and exact to enable those skilled in the art to practice the invention, the physical embodiments herein disclosed merely exemplify the invention which may be embodied in other specific structure. While the preferred embodiment has been described, the details may be changed without departing from the invention, which is defined by the claims.

Figure 1:
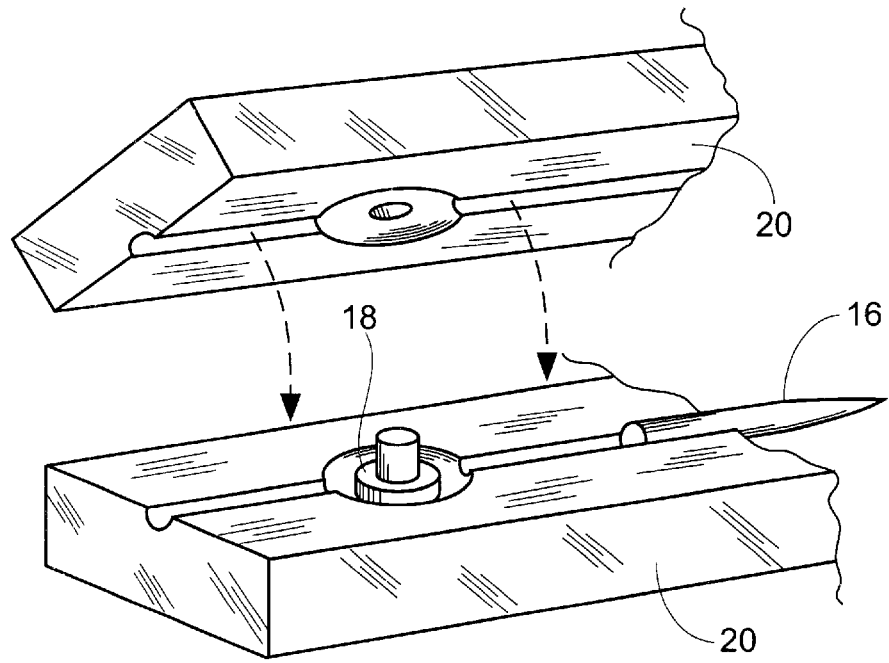
FIG. 1 is a perspective view of a mold used to form the combination suture thread and crimpable lock opening and with a non-reactive, pre-formed toroid in place in the mold and ready to become formed with the thread.
Figure 2:
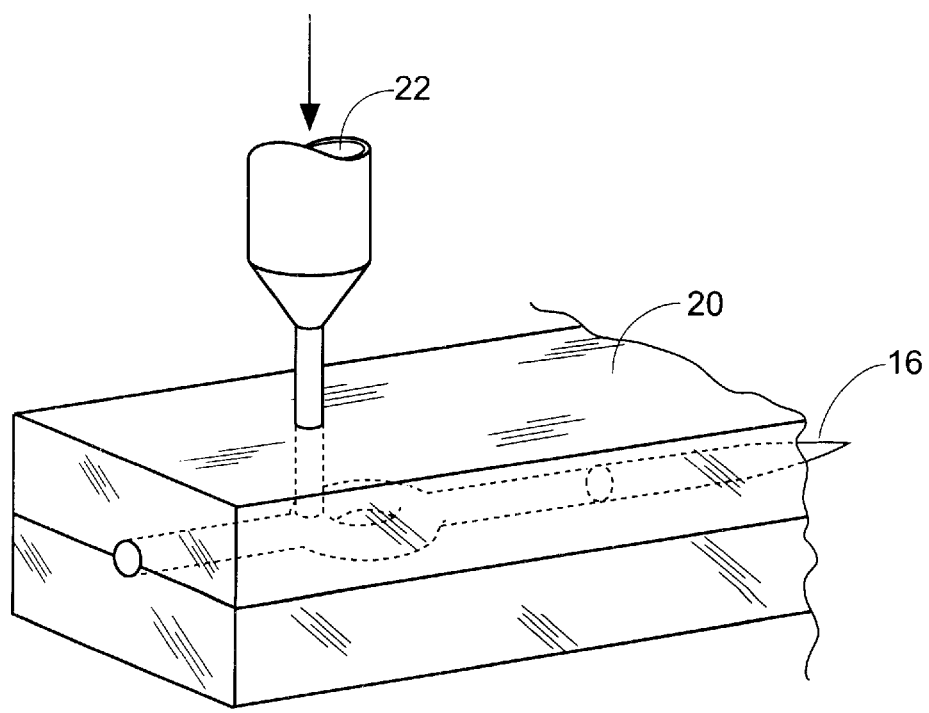
FIG. 2 is a perspective view, partially in phantom, of a mold used to form the combination suture thread and crimpable lock opening, and showing a forming material being filled into the mold.

The preferred embodiment of the molded, one piece, combination suture thread with crimpable lock opening is noted generally by the reference numeral 10. As seen particularly in FIG. 3, the combination device 10 preferably includes a suture thread portion 12 and a crimpable toroid 13 having an opening 14. The molded combination suture 10 may be further provided with a surgical needle 16 which may be either permanently or impermanently attached in a manner known in the art, such as the impermanently attached "pop off" needle. The embodiment illustrated in FIG. 3 may be extrusion or injection molded in a two-step process, seen in FIGS. 1 and 2. As illustrated in FIGS. 1 and 2, the crimpable toroid 13 is formed using a pre-formed annular structure 18 and independently of the molded combination suture 10 seen in the views of FIGS. 3–5. The pre-formed annular structure 18 may be made of titanium, polyglycolate, a VICRYL brand type material, Polyglactin 910, or other suitable material evident to a person skilled in the art, and is coated within the molding material 22. The pre-formed structure 18 is preferably of toroidal configuration and is placed in the suture lock mold 20. The molded combination suture 10 with crimpable opening 14 is formed around the pre-formed structure 18, as the combination suture mold 20 is filled with moldable material 22. The moldable material 22 may be an organic material, plastic derivative, polygalaxon, or other suitable material known to one skilled in the art. Referring further to FIGS. 1 and 2, a suture mold 20 of the type used to mold the combination suture 10 of the present invention is shown. The non-reactive pre-formed structure 18 of the type to be used to form the crimpable opening 14 is shown in FIG. 1 prior to being molded integrally with the suture 10. As seen in FIG. 2, after the pre-formed structure 18 is placed in the mold 20, the material 22 from which the combination suture 10 is to be molded is poured, or injection fed, into the mold 20 and surrounding the pre-formed toroidal structure 18. After an initial setting period, the mono-filament, combination suture 10, with the pre-formed structure 18 disposed within, is removed from the mold 20 and set aside for final cure.

Figure 3:
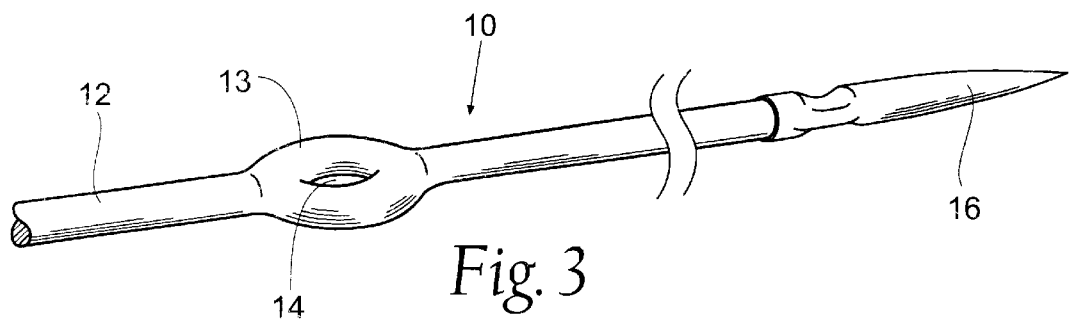
FIG. 3 is a perspective view of the combination suture thread with needle attached.
Figure 4:
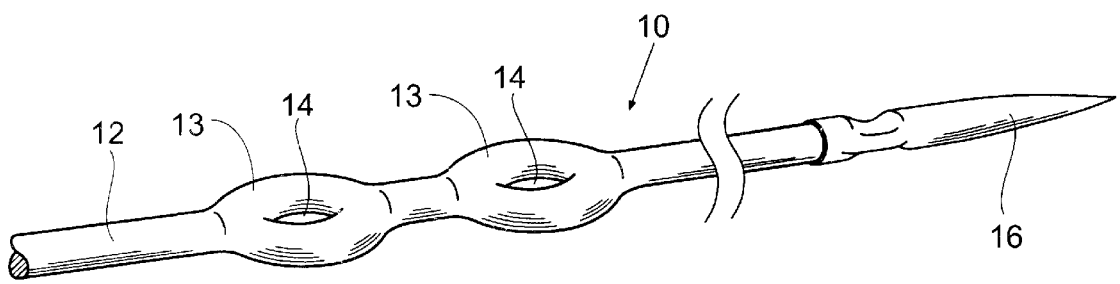
FIG. 4 is a perspective view of an alternate embodiment moldable combination suture thread showing two longitudinally spaced, crimpable openings.
Figure 5:
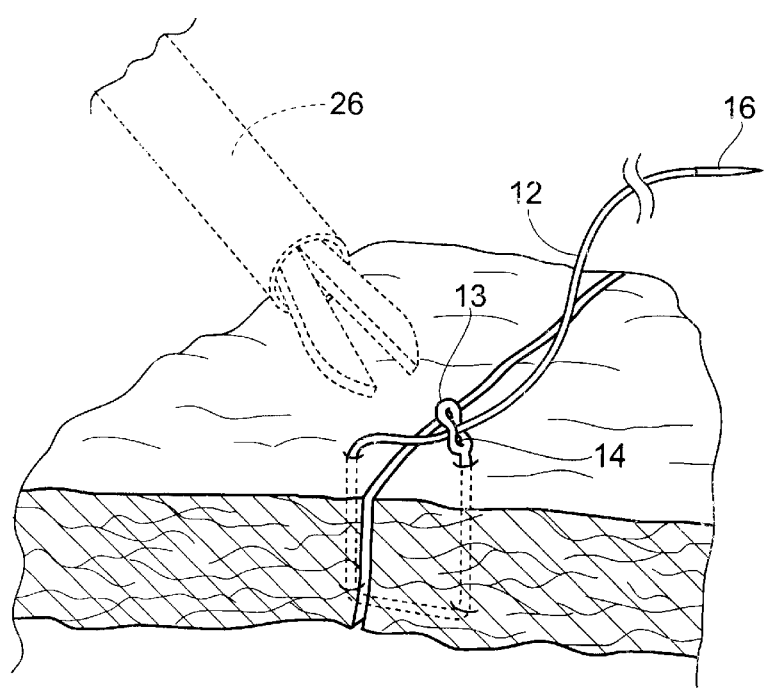
FIG. 5 shows the combination suture thread and crimpable opening of the present invention being used to suture two flaps of tissue.

Referring generally to FIG. 3, the molded suture 10, includes an integrally formed crimpable thread opening 14 and pre-selected thread length 12. The diameter of the crimpable thread opening 14 is slightly larger than the diameter of the integrally formed suture thread portion 12. In the embodiment, shown in FIG. 3, a single crimpable toroid 13 and thread opening 14 is presented. One, or a series, or plurality, of spaced apart crimpable openings 14 may be integrally molded in the suture thread portion 12. FIG. 4 illustrates the present invention having a series of longitudinally spaced crimpable toroids 13 and openings 14 integrally molded in the molded combination suture 10. As seen in FIG. 5, the needle 16 may, after passing through the desired tissue to be sutured, be drawn through a crimpable opening 14 a distance suitable to the surgeon making the stitch and then the crimpable opening 14 is crimped with a crimping tool known in the surgical art (shown in phantom and referenced as 26), thereby locking the suture thread portion 12 in place without the necessity of tying a knot.

Figure 6:
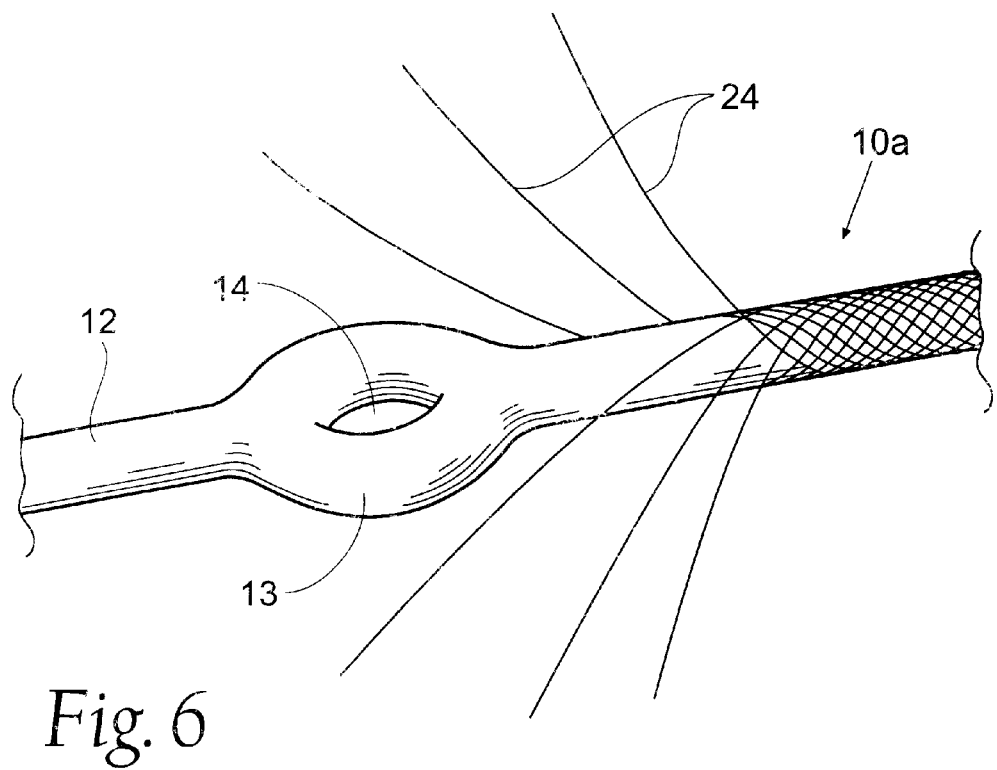
FIG. 6 illustrates an alternate embodiment wherein the combination suture thread with crimpable opening is shown partially covered with multi-ply filaments.
Figure 7:
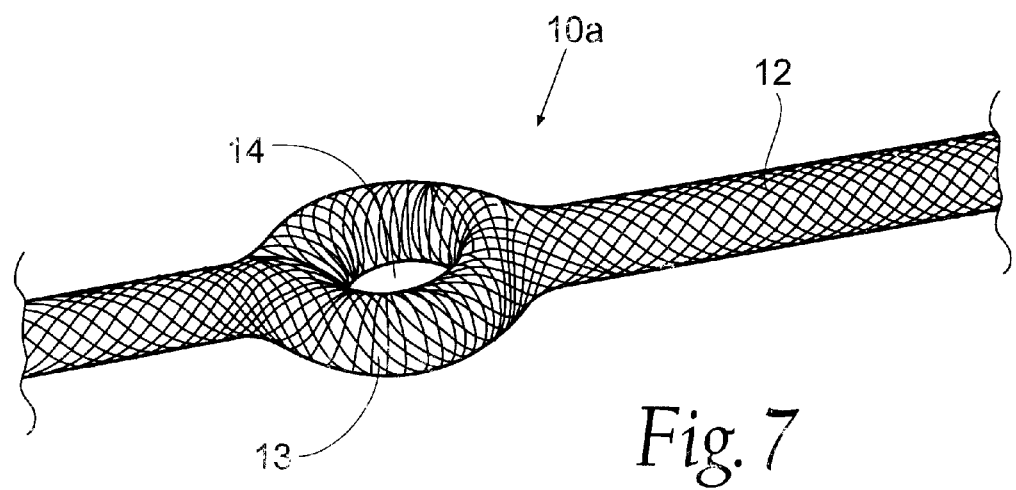
FIG. 7 illustrates the alternate embodiment seen in FIG. 6, and wherein the combination suture thread and crimpable opening is covered with multi-ply filament.

An alternate embodiment combination suture thread 10a, may be seen in FIGS. 6 and 7. In this embodiment, the one-piece, combination suture thread with crimpable lock opening 10 is molded as illustrated and described with reference to FIGS. 1 and 2, however after the initial molding process, the alternate embodiment shown in FIGS. 6 and 7 is additionally braided (as seen in FIG. 6) with a series of mono-filaments 24, to thereby create a multi-strand combination suture thread with crimpable opening, 10a. The braided device 10a seen in FIGS. 6 and 7 offers the added benefit of friction resistance against pull out of the thread portion 12 once passed through the desired tissue to be sutured.

Figure 8:
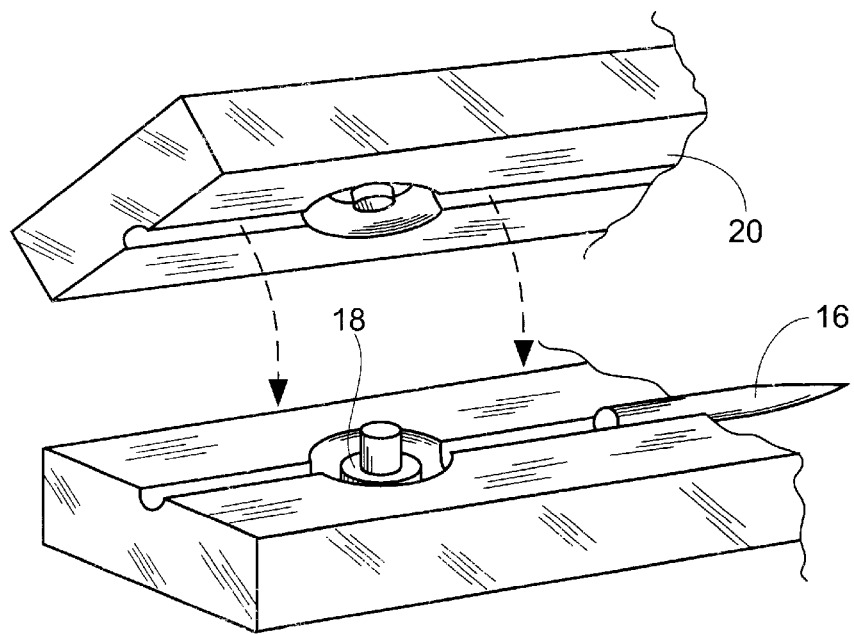
FIG. 8 is a perspective view of a mold used to form an alternate embodiment crimpable suture thread having two superposed, crimpable openings and with non-reactive annular structure or washers in place in the mold and ready to become formed with the thread.
Figure 9:
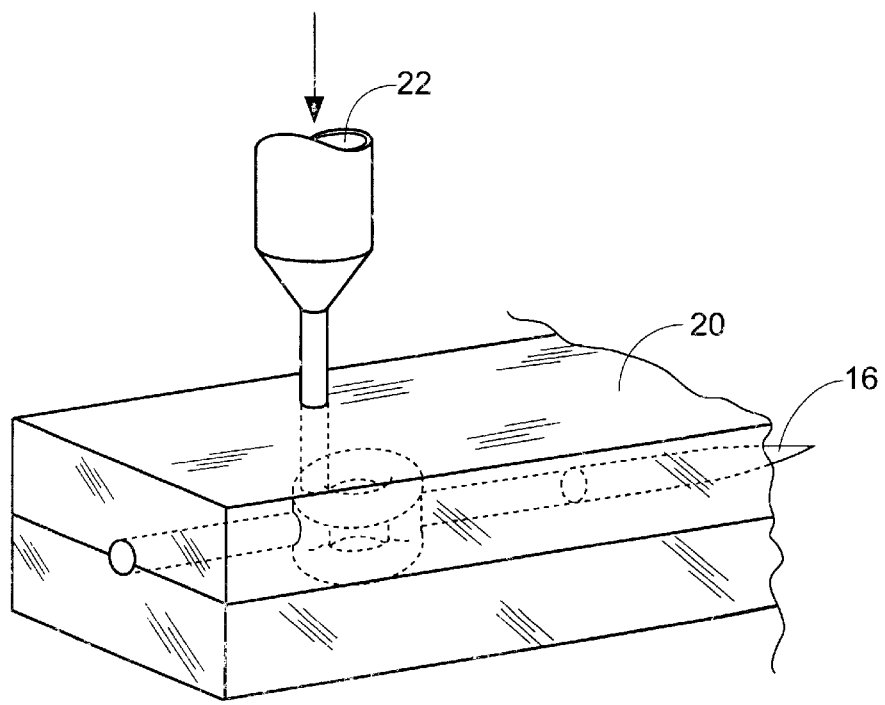
FIG. 9 is a perspective view, partially in phantom, of a mold used to form the alternate embodiment crimpable suture lock of FIG. 8, and showing a forming material being filled into the mold.
Figure 10:
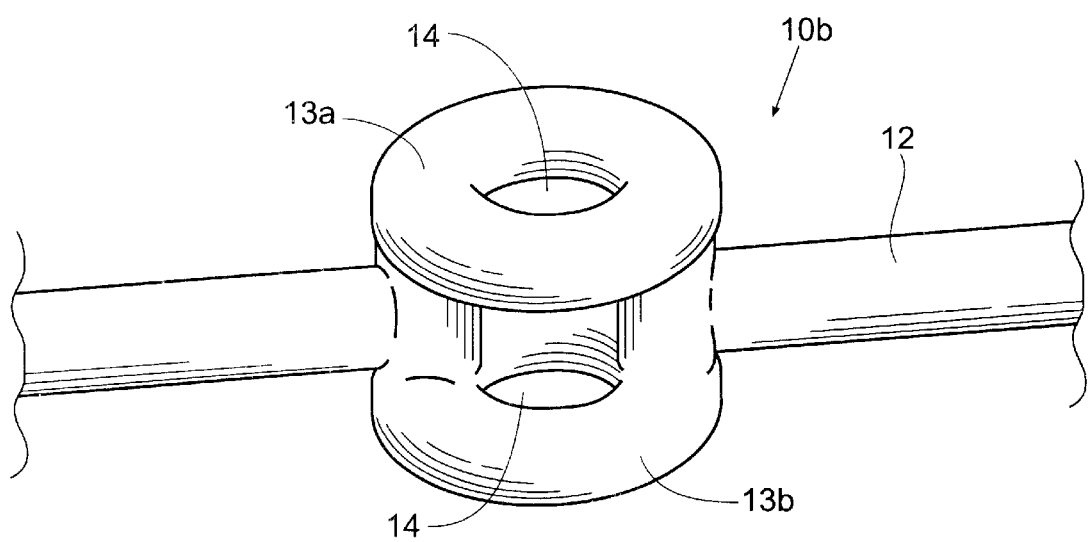
FIG. 10 is a perspective view of the alternate embodiment seen in FIGS. 8 and 9, and showing two superposed crimpable openings.

Referring now to FIGS. 8–10, a design similar to that of FIGS. 1–3 is illustrated except a plurality of pre-formed toroidal structures 18 is molded in a stacked or superposed configuration. This alternate embodiment combination suture thread is referenced generally as 10b, and as viewed in FIGS. 8–10, feature a plurality of crimpable toroids 13a, 13b. Seen a particularly in FIGS. 8 and 9, pre-formed structures 18 are molded in a stacked or superposed configuration such that multiple crimpable openings 14 are presented and wherein multiple crimps may be made along the suture thread portion 12. The combination suture thread 10b may be attached either permanently or impermanently to a surgical needle (as seen in FIGS. 3 and 4) in a manner known in the art. Again, a needle 16 may, after passing through the tissue to be sutured, be drawn through one of the openings 14, and, after forming a stitch may be passed through a second opening 14, thereby allowing multiple crimps along a single stitch length. An advantage of this embodiment is that a single combination suture thread 10b may serve to lock the suture thread portion 12 multiple times. Similarly to the embodiment illustrated in FIGS. 6 and 7, the embodiment shown in FIGS. 8–10 may be further braided with a series of monofiliments thereby forming a multi-strand structure (not shown in these views).

The foregoing is considered as illustrative only of the principles of the invention. Furthermore, since numerous modifications and changes will readily occur to those skilled in the art, it is not desired to limit the invention to the exact construction and operation shown and described. While the preferred embodiment has been described, the details may be changed without departing from the invention, which is defined by the claims.

What is claimed is:

1. A suturing apparatus comprising an integrally molded suture thread and crimpable structure wherein said crimpable structure defines an opening arranged to receive said thread and said opening being crimpable upon said thread, and wherein said crimpable structure comprises an enclosed toroidal configuration.

2. The integrally molded suture thread and crimpable structure of claim 1, wherein said structure is further comprised of a multi-strand outer surface.

3. The integrally molded suture thread and crimpable structure of claim 1 further including a plurality of crimpable structures.

4. The integrally molded suture thread and crimpable structure of claim 3, wherein said plurality of crimpable structures are arranged in superposed condition.

5. The integrally molded suture thread and crimpable structure of claim 3, wherein said plurality of crimpable structures are longitudinally spaced apart.

6. A method of making an integrally molded suture thread and crimpable structure, the method comprising the steps of:

placing a pre-formed annual structure in a mold;

filling said mold with a moldable material;

allowing said moldable material to cure; and removing said integrally molded suture thread and crimpable suture from said mold.

7. The method of claim 6 further comprising the step of attaching a surgical needle to one end of said suture thread.

8. The method of claim 6 further comprising the step of braiding said suture thread with one or more monofilaments.

9. The method of claim 8 further comprising the step of attaching a surgical needle to one end of said suture thread.

* * * * *